United States Patent [19]
Yoshitome et al.

[11] Patent Number: 5,732,701
[45] Date of Patent: Mar. 31, 1998

[54] DATA COLLECTION METHOD FOR MR ANGIOGRAPHY

[75] Inventors: Eiji Yoshitome; Yoshikazu Ikezaki, both of Hino, Japan

[73] Assignee: GE Yokogawa Medical Systems, Limited, Tokyo, Japan

[21] Appl. No.: 581,821

[22] Filed: Jan. 2, 1996

Related U.S. Application Data

[63] Continuation-in-part of Ser. No. 244,060, filed as PCT/JP92/01637, Dec. 16, 1992, abandoned.

[51] Int. Cl.$^6$ .................................................. A61B 5/055
[52] U.S. Cl. .................... 128/653.2; 324/307; 324/309
[58] Field of Search .............................. 128/653.2, 653.3; 324/306–309

[56] References Cited

U.S. PATENT DOCUMENTS

| | | | |
|---|---|---|---|
| 4,715,383 | 12/1987 | Ehman et al. | 128/653.2 |
| 4,937,526 | 6/1990 | Ehman et al. | 324/309 |
| 5,297,551 | 3/1994 | Margosian et al. | 128/653.2 |
| 5,368,033 | 11/1994 | Moshfeghi | 128/653.2 |

*Primary Examiner*—Brian L. Casler
*Attorney, Agent, or Firm*—Moonray Kojima

[57] ABSTRACT

A data collection method for MR angiography, wherein the scans resulting in spin warp values are assigned into groups of two or more consecutive acquisitions and each group is averaged two or more times for each heart beat period, whereby data collection time is reduced concurrently with suppression of motion artifacts, all without use of additional hardware.

3 Claims, 4 Drawing Sheets

5,732,701

DATA COLLECTION METHOD FOR MR ANGIOGRAPHY

RELATED APPLICATIONS

This is a continuation in part of U.S. Ser. No. 08/244,060 filed May 13, 1994, which originated from PCT/JP92/01637 filed Dec. 15, 1992, now abandoned.

BACKGROUND OF THE INVENTION

1. Field of Invention

This invention relates to a data collection method for Magnetic Resonance (MR) angiography; and more particularly, to such method wherein motion artifacts are substantially suppressed by averaging data obtained from multiple acquisitions.

2. Description of the Prior Art

FIGS. 4 and 5 show prior art data collection methods for MR angiography, wherein motion artifacts are suppressed to some degree by averaging data obtained from multiple acquisitions. One such method is described by C. Dumoulin et al in "Rapid Scan Magnetic Resonance Angiography" (Mag. Reson. Med. 1987, 5: 238–45)(called Disclosure 1). Another disclosure of the "Rapid Scan NMR angiography" is contained in U.S. Pat. No. 4,800,889 issued to Dumoulin et al on Jan. 31, 1989 (called Disclosure 2). Both of these disclosures are incorporated herein in their entirety by reference.

FIG. 4 shows the method of Disclosure 1, wherein the number of data acquistions "n" of scan time TR, is averaged once per time period "t", with "t" being approximately the heartbeat period "T". That is, the number "n" is the closest integer to the value of [(heart beat period T)/(scan time TR)] or for a typical case of scanning time of TR=⅛second, and heartbeat period T=1 second, "n" equals 8. Thus, there will be 8 acquistions of data or scans per a time period which is equal to about the heart beat period. The number of data acquisitions or scans resulting in echoes are labeled "warp value" in FIGS. 3,4 and 5, to represent the results of a warp procedure of imaging, such as described in Disclosure 1, at page 239. Thus, in FIG. 14, the value of 8 acquistions, labeled #1, are averaged once per time period "t", which is close to the heart beat period "T". Then, the next group of acquisitions, which are labeled as warp value #2, are averaged once per time period "t". The blood flow rate which is averaged over the time period "t", is thus, the average blood flow rate for one heart beat period "T". Hence, no substantial motion artifacts are produced in the reconstructed image.

However, there is a problem with the prior art method just discussed in that since the averaging period "t" is about one heart beat period "T", which is about one second in practice, the time required to collect 256 groups of scans (the number 256 is generally that for one frame of a reconstructed image, as is known in the art) would be 256 seconds, or about 4 minutes, which is a long period of time to expect a subject being examined to remain immobile. If the subject moves during the examination, there will be other artifacts which turn up on the image.

If the number"n" of acquisitions in one group to be averaged can be decreased, for example, to two, as shown in FIG. 5, and t=2TR, then the entire data collection time can be reduced. However, on the flip side of that method is that the average blood stream flow would be taken over a period of less than one heart beat. Thus, motion artifacts will be present in the reconstructed image. Note in Disclosure 1, notation "n" is recited as "a", but has been changed herein to "n" to improve clarity.

Thus, in the conventional art methods, there is a dilemna.. either the data collection time is reduced with greater motion artifacts, or data collection time is increased with less motion artifacts, but, in the art, there is no method wherein the data collection time is reduced with concurrent substantial suppression of motion artifacts without having any added hardware.

SUMMARY OF THE INVENTION

Accordingly, an object of the invention is to overcome the aforementioned and other deficiencies and disadvantages of the prior art.

A further object is to improve upon the averaging method for suppressing motion artifacts in the MR angiography method, so that concurrently, the motion artifacts are suppressed and the collection time is reduced without the necessity of adding hardware to the existing apparatus.

The foregoing and other advantages, features and objects are attained in the invention by a data collection method for MR angiography, wherein the number of data acquistions with scan period TR is averaged a number of times more than once per period of time "t" which is equal to substantially the heartbeat time "T", whereby the number of times the data acquisitions can be averaged per time period "t" can be selected arbitrarily and is two or more, with the time period "t" being close to the heartbeat period "T", so that motion artifacts are substantially suppressed and data collection time is substantially reduced all without increasing the hardware used in such data collection apparatus.

DETAILED DESCRIPTION OF PREFERRED EMBODIMENTS

Figure 1:
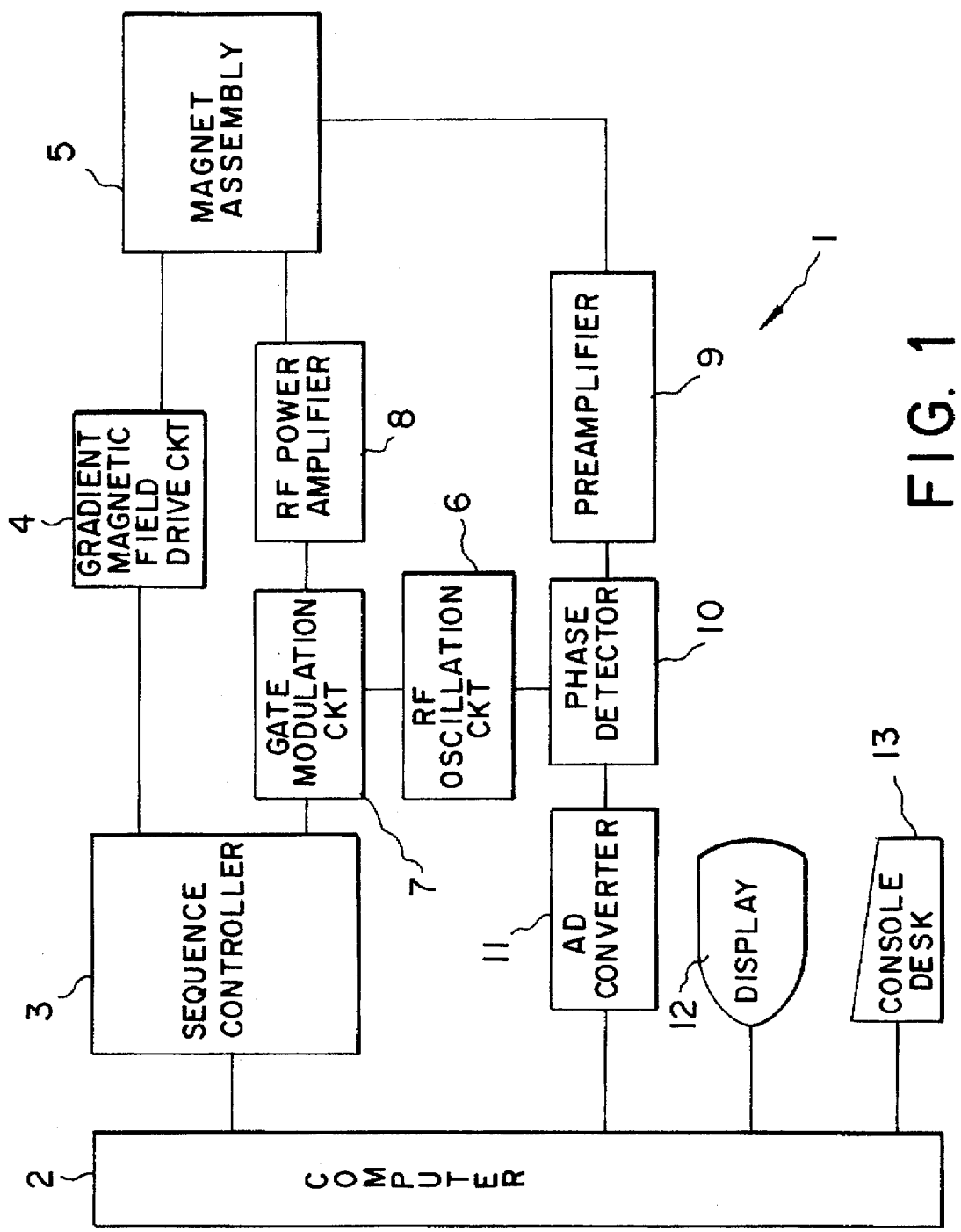
FIG. 1 is a block diagram depicting an MRI apparatus for carrying out the method of the invention.

FIG. 1 shows an MRI (magnetic resonance imaging) apparatus 1 for carrying out the invention comprising a computer 2 connected to sequence controller 3, analog-to-digital (AD) converter 11, display 12, and console desk 13. Sequence controller 3 is connected to gradient magnetic field drive circuit 4, and gate modulation circuit 7, which is connected to RF power amplifier 8 and RF oscillation circuit 6, which is connected to phase detector 10, which is connected between AD converter 11 and preamplifier 9. Magnetic assembly 6, within which is contained a space for holding the subject being examined, is driven by gradient magnetic circuit 4 and RF power amplifier 8, and the reflected signals are then picked up and amplified by preamplifier 9, which is connected to phase detector 10.

Computer 2 controls the system based on commands from console 13. Controller 3 operates drive circuit 4, based on stored sequence so that a gradient magnetic field is generated in a static magnetic field space located within gradient magnetic field coils within magnetic assembly 5. The controller 3 also controls gate modulation circuit 7 so that RF pulses generated by RF oscillation circuit 6 is modulated into prescribed waveforms and is applied through RF power amplifier 8, to a transmission coil located within magnetic assembly 5. The transmission coil forms an RF magnetic field in the static magnetic field space within the magnetic assembly 5.

Nuclear magnetic resonance (NMR) signals obtained from the subject being examined by a reception coil also located within magnetic assembly 5, is applied then through a preamplifier 9 to a phase detector 10, and then further applied through the AD converter 11 to computer 2. Computer 2 then reconstructs an image of the subject, e.g. blood flow and tissues, based on the data of the NMR signals received from converter 11, and then causes display of the reconstructed image on display 12. The foregoing description is generally that of an NMR system.

Figure 2:
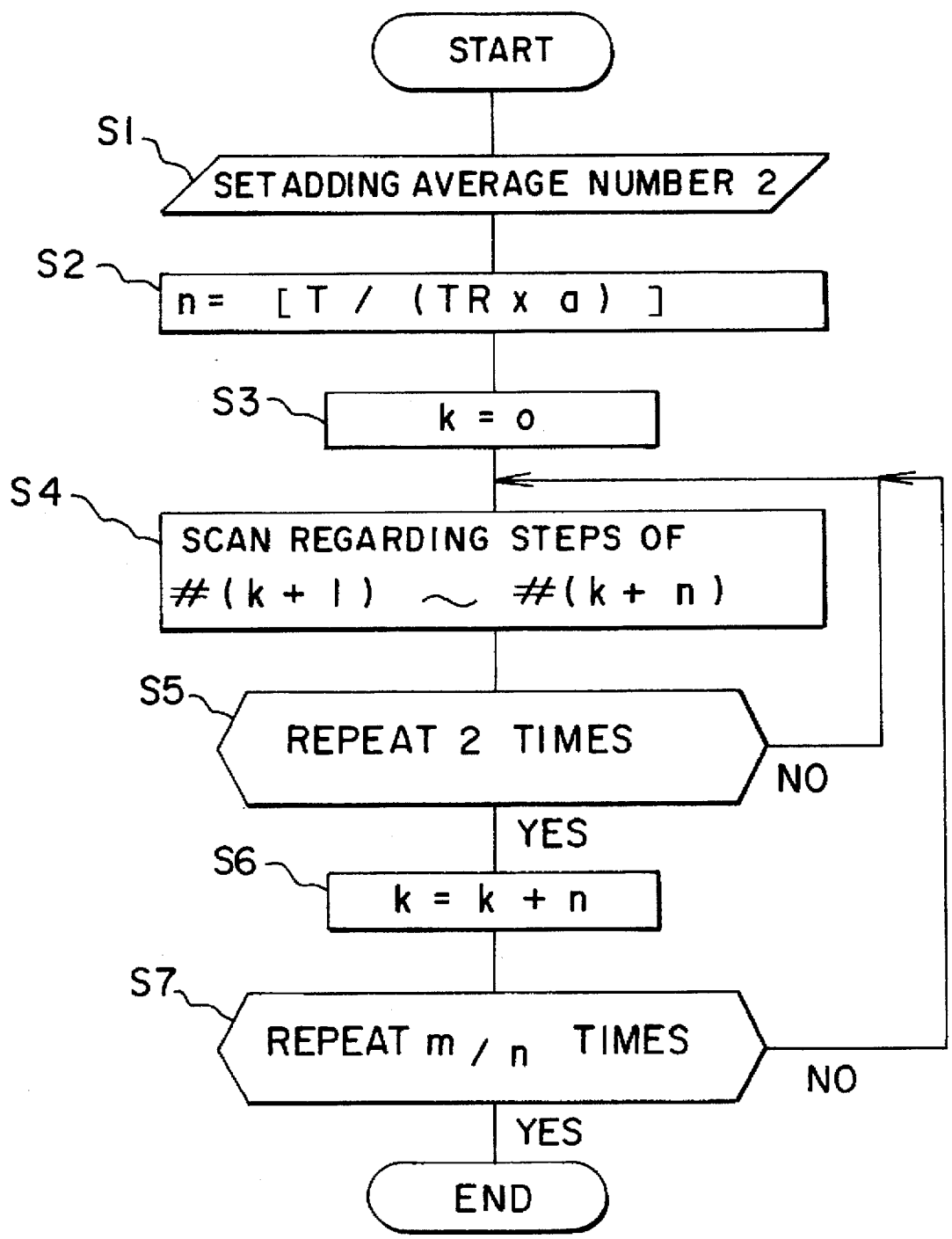
FIG. 2 is a flow chart depicting the method steps for collecting data for the MR angiography of the invention.
Figure 3:
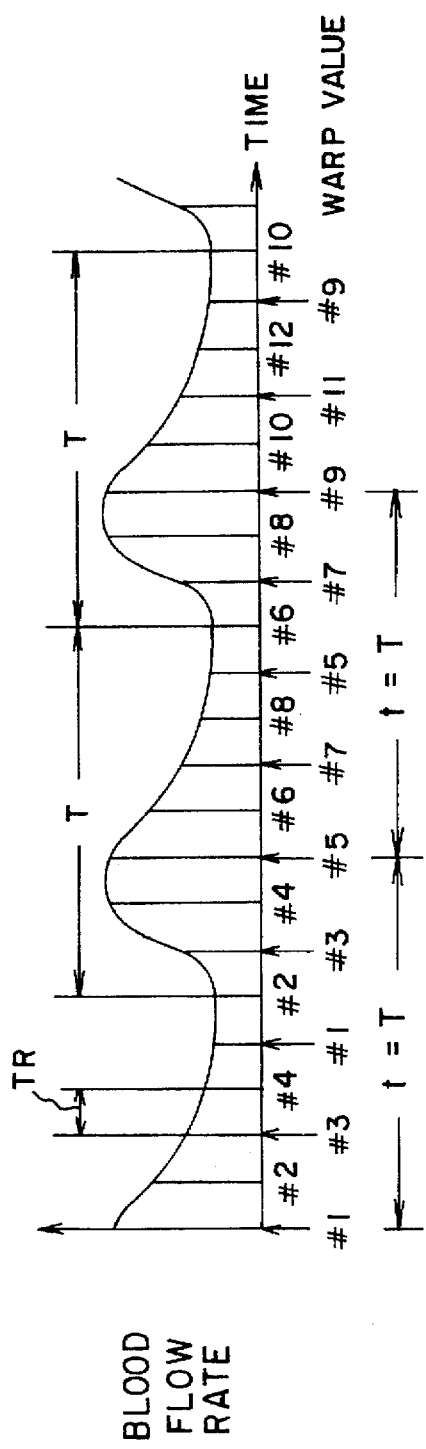
FIG. 3 is a wave chart depicting scan timing according to the invention.
Figure 4:
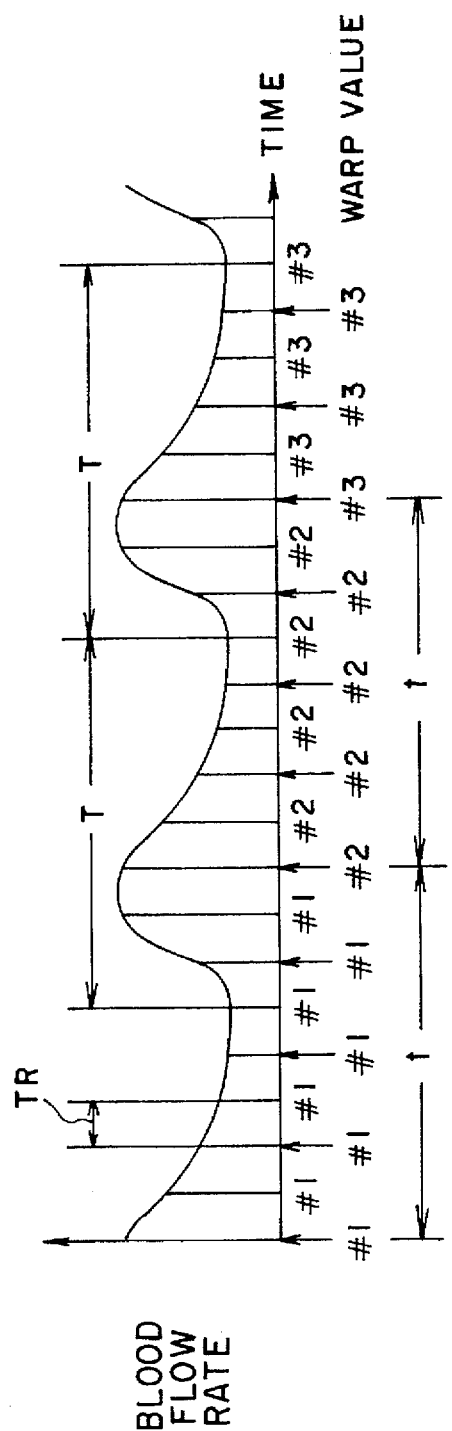
FIGS. 4 and 5 are diagrams depicting scan timing according to prior art data collection methods for MR angiography.
Figure 5:
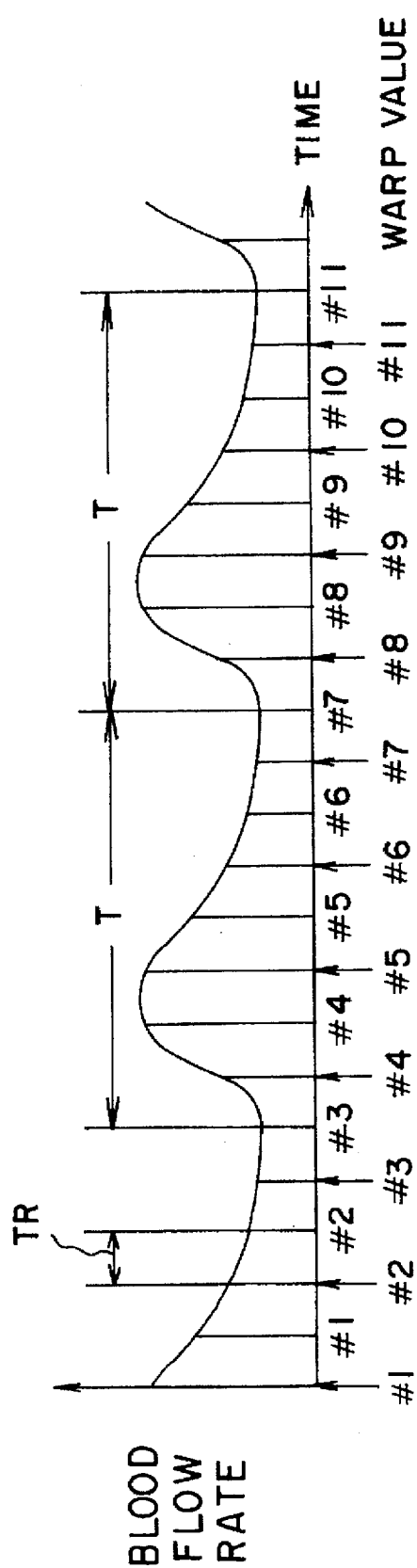

The data collection method of the invention is executed by a procedure stored in computer 2 and sequence controller 3, such procedures are discussed below with reference to FIGS. 2 and 3, which show the steps and timing of scans of the data collection method of the invention. The method steps comprise the following, as shown more specifically in FIG. 2:

STEP S1 A human operator using console desk 13 arbitrarily sets a number of times "a" that the acquisitions in a group are to be averaged for each time period "t" (called "adding average number" 'a' in STEP S1 of FIG. 2).

STEP S2. Integral "n" which is closest to the result of [(heart beat period T)/(scan time TR×number of times "a")] is calculated. This number "n" is the number of data acquisitions in a group which is to be averaged. For example, if the heart beat period "T" is one second, and the repeat time TR is 1/8second, and the number of times "a" a group of scans is averaged per time period "t" is two, then "n" is calculated to be 4. For example, in FIG. 3, the number of acquisitions is shown as #1, #2, #3, #4, that is then the number "n" is four. This group of 4 scans is averaged, and then the next group of acquisitions #1, #2, #3, #4 is then averaged. That is to say, the number of times "a" each group of scans is averaged per time "t" is two. The next group of 4 scans is labelled as #5, #6, #7, #8, which is then averaged, and then the next group of 4 scans being #5, #6, #7, #8 is then averaged, such averaging number of times "a" being twice per unit time "t", or in this case, twice per heart beat period.

STEP S3. The scanning step "k" is set to be zero.

STEPS S4, S5. At first, scanning steps #1, #2, #3, #4 (that is K+1 to K+4, or 0+1 to 0+4, becomes 1 to 4) is repeated "a" times, i.e. twice since that is the number of times each group of scans will be averaged during the time "t". In this example, in FIG. 3, the scanning steps #1, #2, #3, #4 (i.e. n=4) is repeated twice (i.e. a=2) for each time period "t", and then for the next group of acquisitions, #5, #6, #7, #8 (i.e. n=4), the averaging is repeated again twice (i.e. a=2) for each time period "t". In this example, the time "t" is substantially equal to the heart beat period "T".

STEP S6. The number of scanning steps is set to be k=k+n. At first, when k=0, k becomes n. For example, in the foregoing example, k becomes 4.

STEP S7. The above steps S4–S6 are repeated m/n times, wherein "m" is the number of slices used for a frame of image. In most cases, as well known, "m" is 256. Thus, where m=256, the repeated steps will be 256/4=64.

Accordingly, the averaging which eliminates the motion artifacts is done without having to use up the time otherwise required for the usual 256 slices, or about 4 minutes. In the invention, the foregoing use of "a"=2, of the number of acquisitions being "n"=4, per time cycle "t", the scanning to obtain a motion artifact-free image can be done in a substantially less time, that is only 64 seconds, which is a considerable improvement over the prior art.

Since the scan resulting in the same spin warp value is carried out such that the heart beat period "T" is equally divided by the number of groups of each time period which is averaged, that is by the number "a", variations in the blood flow rate during one heart beat is cancelled by averaging the measured data over at least one heart beat period and the blood flow rate becomes equivalent to the average blood flow rate. Since the condition is the same in each scanning step, no difference in blood flow rate will occur between the acquisitions, and a good image will be produced without any substantial motion artifacts. Also, data collection time is reduced by the number of times the scan averaging is carried out in one heart beat period. These two advantageous results are attained without having to increase the number of hardware that is required.

The foregoing description is illustrative of the principles of the invention. Numerous extensions and modifications thereof would be apparent to the worker skilled in the art. All such extensions and modifications are to be considered to be within the spirit and scope of the invention.

What is claimed is:

1. In a data collection method of MR angiography, wherein a specimen fluid driven at a heartbeat rate "T" and being examined is exposed to a magnetic field and scanned at a repetition rate "TR", and data of the fluid flow rate of the fluid is obtained by encoding detected echoes of magnetic resonance of the fluid produced by the scanning, and multiple scanned data are averaged over a selected period "t", and the averaged scanned data are used to reconstruct an image of the specimen fluid; the improvement comprising the steps of (A) selecting arbitrarily a number "a" of times to average a number of data scans "n" over the selected time period "t", wherein "t" is selected to be substantially equal to the heartbeat rate "T";

(B) calculating number "n" of scans which are to be averaged using the formula;

(C) taking an average of the number "n" of scans;

(D) repeating the averaging of "n" scans a number of times "a" for each selected time period "t"; and (E) repeating the foregoing steps (C) and (D) a number of times "m" equal to number of lines of pixels desired in a reconstructed image; whereby motion artifacts are substantially eliminated from a reconstructed image and data scan time is reduced without use of added hardware.

2. The method of claim 1, wherein said number "n" is 4, and said number "a" is 2.

3. The method of claim 1, wherein said steps (C) and (D) are repeated a number of times equal to m/n.

* * * * *